United States Patent [19]

Nissen et al.

[11] 4,146,581

[45] Mar. 27, 1979

[54] MANUFACTURE OF HIGHER KETONES

[75] Inventors: Axel Nissen, Leimen; Otto Woerz; Gerd Heilen, both of Ludwigshafen; Werner Fliege, Otterstadt; Arnold Wittwer, Ludwigshafen, all of Fed. Rep. of Germany

[73] Assignee: BASF Aktiengesellschaft, Ludwigshafen, Fed. Rep. of Germany

[21] Appl. No.: 782,637

[22] Filed: Mar. 30, 1977

[30] Foreign Application Priority Data

Apr. 8, 1976 [DE] Fed. Rep. of Germany ....... 2615308
Jun. 5, 1976 [DE] Fed. Rep. of Germany ....... 2625540

[51] Int. Cl.$^2$ .......................... C07B 5/02; C07C 27/04; C07C 29/14; C07C 45/00

[52] U.S. Cl. ............................... 260/586 C; 252/443; 252/462; 260/590 E; 260/593 R; 260/598; 260/599; 260/600 R; 260/601 R; 260/682; 568/799; 568/814; 568/881; 568/648; 568/579; 568/671

[58] Field of Search ........... 260/586 C, 590 E, 593 R, 260/592

[56] References Cited

U.S. PATENT DOCUMENTS

| | | | |
|---|---|---|---|
| 2,443,732 | 6/1948 | Ipaheff et al. .................... | 260/586 C |
| 2,549,508 | 4/1951 | Mottern ............................ | 260/586 C |
| 3,248,428 | 4/1966 | Porter et al. ..................... | 260/586 C |
| 3,316,303 | 4/1967 | Mertzeweiller et al. .......... | 260/586 C |
| 3,379,766 | 4/1968 | Hwang et al. ................... | 260/593 R |
| 3,542,878 | 11/1970 | Swift ............................... | 260/586 C |
| 3,746,733 | 7/1973 | Stapfer et al. ................... | 260/586 C |
| 3,876,706 | 4/1975 | Tevaneosky et al. ........... | 260/586 C |
| 3,946,079 | 3/1976 | Mizutani et al. ................. | 260/586 C |
| 3,948,991 | 4/1976 | Chum et al. ...................... | 260/593 R |
| 4,005,147 | 1/1977 | Fischer et al. ................... | 260/590 E |

FOREIGN PATENT DOCUMENTS

| | | |
|---|---|---|
| 1238453 | 4/1967 | Fed. Rep. of Germany. |
| 1917244 | 10/1970 | Fed. Rep. of Germany. |
| 2022365 | 11/1970 | Fed. Rep. of Germany. |
| 2023512 | 2/1971 | Fed. Rep. of Germany. |
| 1936203 | 9/1971 | Fed. Rep. of Germany. |
| 2257675 | 5/1974 | Fed. Rep. of Germany. |
| 1530898 | 7/1967 | France. |
| 1579809 | 8/1969 | France. |
| 2019319 | 7/1970 | France. |

OTHER PUBLICATIONS

Eschinazi, "Bull Soc. Chim," 1952: 967–969, (1952).

*Primary Examiner*—Norman Morgenstern
*Attorney, Agent, or Firm*—Keil & Witherspoon

[57] ABSTRACT

A process for the manufacture of higher ketones by reacting an aldehyde with a ketone in the presence of hydrogen over a catalyst system which contains, firstly, oxides or salts of the rare earth metals and, secondly, metals of group VIII of the periodic table of the elements. The process gives numerous higher ketones, required, for example, as solvents for surface coatings, or as scents, with high conversions and good selectivities, and therefore more simply and more economically than conventional methods.

14 Claims, No Drawings

MANUFACTURE OF HIGHER KETONES

The present invention relates to a process for the manufacture of higher ketones by reacting an aldehyde with a ketone in the presence of hydrogen over a catalyst system which contains, firstly, oxides or salts of the rare earth metals and, secondly, metals of group VIII of the periodic table of the elements.

The production of saturated higher carbonyl compounds by dimerizing acetone or other ketones or dimerizing aldehydes under hydrogenating conditions, in a single process step, has been disclosed.

In industrial operation, this process is preferably effected with fixed bed catalysts because the reaction may in this way be carried out more simply. Reactions in both the gas phase and the liquid phase have been disclosed, a reaction in the liquid phase being preferred because of the longer catalyst life thereby achievable, which is of importance particularly if expensive catalysts, for example catalysts containing noble metal components, are used.

The following patents and patent applications may be cited, by way of example, in this context: German Laid-Open Application DOS No. 2,023,512, German Laid-Open Application DOS No. 2,022,365, German Pat. No. 1,238,453, French Pat. No. 1,530,898, French Pat. No. 1,579,809, German Pat. No. 1,936,203, German Pat. No. 1.951,357, French Pat. No. 2,019,319 and U.S. Pat. No. 3,379,766.

The literature rarely provides experimental data on selective reactions of aldehydes with ketones under condensing/hydrogenating conditions.

U.S. Pat. No. 3,316,303 discloses the manufacture of higher ketones by reacting lower ketones with aldehydes which only have 1 H atom alpha to the carbonyl group, in the presence of an oil-soluble condensing catalyst which contains a metal of group II of the periodic table, lead, manganese or cobalt, and a hydrogenating catalyst, e.g., molybdenum sulfide, nickel or mercury, or a cobalt carbonylation catalyst. This patent states that aldehydes which contain more than 1 H atom alpha to the carbonyl group cannot be reacted with ketones since the dimer aldehyde forms more readily than the aldehyde/ketone condensate. However, even in the case of the reaction, described in the said patent, of ketones with an aldehyde having only one alpha hydrogen atom, the desired higher ketones are only obtained with rather low selectivities. For example, the reaction of 2-methyl-propanal with acetone is said to give methyl isoamyl ketone with only about 45 percent selectivity based on acetone and only about 25 percent selectivity based on 2-methyl-propanal, the conversion being about 55% based on acetone.

The composition of the reaction products shows clearly the causes of the poor selectivity with which methyl isoamyl ketone is obtained in this reaction.

1. Substantial hydrogenation of the carbonyl compounds employed, to give alcohols, occurs, and the carbonyl compounds are thus lost as far as the aldol reaction is concerned (selectivity for isopropanol or acetone ~ 30%).

2. About 25% of the reaction product consists of higher-boiling constituents which have been identified as secondary products of acetone, resulting from autocondensation. In Example VII of the above patent, the bottoms amount to as much as 53%. This side-reaction becomes the more serious if, for technical reasons, an excess of acetone has to be used.

Since many of the reaction products obtainable by condensing aldehydes with ketones under hydrogenating conditions are of great interest — examples include methyl isoamyl ketone, a popular solvent in the surface-coatings industry and an intermediate product for chemicals used in rubber processing, and 4-phenyl-butan-2-one, used as a scent — it is an object of the invention to provide a catalyst system which makes it possible to condense aldehydes and ketones to higher ketones under condensing-hydrogenating conditions, with good selectivities, i.e. avoiding the formation of substantial amounts of alcohols by hydrogenation of carbonyl groups, and avoiding the formation of substantial amounts of higher-boiling dimerization products of the individual carbonyl compounds.

We have found, surprisingly, that this object is achieved and that ketones and aldehydes can be reacted in the presence of $H_2$, to give higher ketones, i.e., ketones having 5 or more carbon atoms, with very good selectivities, if the reaction is carried out in the presence of a catalyst system which contains metals of group VIII of the periodic table of the elements and oxides of the rare earth metals.

Accordingly, the present invention relates to a process for the manufacture of higher ketones by reacting an aldehyde of the general formula I

where $R^1$ is unbranched or branched alkyl of 1 to 20 carbon atoms, preferably of 1 to 8 carbon atoms, and especially of 1 to 5 carbon atoms, aryl or cycloalkyl which are unsubstituted or substituted by lower alkyl, preferably phenyl or cyclohexyl, or aralkyl of 7 to 20 carbon atoms, preferably of 7 to 10 carbon atoms, and the said radicals may also carry hydroxyl or alkoxy groups as inert substituents, with a ketone of the general formula II

where $R^2$ is unbranched or branched alkyl of 1 to 20 carbon atoms, preferably of 1 to 8 carbon atoms, and especially of 1 to 5 carbon atoms, aryl or cycloalkyl which are unsubstituted or substituted by lower alkyl, perferably phenyl or cyclohexyl, or aralkyl of 7 to 20 carbon atoms, preferably of 7 to 10 carbon atoms, and the said radicals may also carry hydroxyl or alkoxy groups as inert substituents, in the presence of hydrogen and a catalyst system which possesses both condensing and hydrogenating properties, at an elevated temperature, in which process the reaction is carried out in the presence of a catalyst system which contains, firstly, an oxide or a salt of the rare earth metals or a mixture of oxides or salts of the rare earth metals and, secondly, one or more metals of group VIII of the periodic table of the elements, at from 80° to 280° C.

It is true that German Laid-Open Application DOS No. 2,257,675 discloses a process for alkylating ketones in the α-position by reacting the ketone with a primary alcohol over catalysts containing metallic copper and/or metallic silver, but using this process higher ketones are obtained either with poor conversions or with poor selectivities, even if the process is carried out in the presence of oxides or hydroxides of the alkali metals and/or alkaline earth metals and/or of the rare earth metals as catalyst promoters.

In contrast, the reaction according to the invention takes place with rather good conversions and good selectivity, in accordance with the equation:

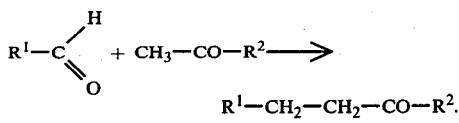

$$R^1-CH_2-CH_2-CO-R^2.$$

The aldehydes of the general formula I, and the ketones of the formula II, required as starting compounds, are well-known commercial compounds.

Examples of suitable aldehydes of the formula I are: acetaldehyde, propanal, butanal, 2-methyl-propanal, 2-methyl-butanal, 3-methyl-butanal, pentanal, 2-methyl-pentanal, 2-ethyl-hexanal, formylcyclo-hexane, benzaldehyde, p-hydroxy-benzaldehyde, p-hydroxy-m-methoxy-benzaldehyde and p-tert.-butyl-benzaldehyde.

Examples of suitable ketone components are acetone, butan-2-one, 3-methyl-butan-2-one, 4-methyl-pentan-2-one, 5-methyl-hexan-2-one, heptan-2-one, methyl cyclohexyl ketone, 4-methoxy-butan-2-one, 4-phenyl-butan-2-one, acetophenone and p-methoxy-acetophenone.

If a ketone which has both a methyl group and a methylene group in the α-position to the carbonyl group is used, aldehyde attacks virtually exclusively the methyl group in the reaction according to the invention. The content of isomeric product resulting from reaction with the methylene group amounts to only about 1–3%.

The catalyst system used according to the invention contains, firstly, an oxide or a salt of the rare earth metals or a mixture of the oxides or salts of the rare earth metals and, secondly, one or more metals of group VIII of the periodic table.

For the purposes of the invention, oxides of the rare earth metals are the oxides of lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb) and lutetium (Lu).

Examples of preferred oxides of the rare earths are: $La_2O_3$, $CeO_2$, $Pr_2O_3Nd_2O_3$, $Sm_2O_3$, $Gd_2O_3$ and $Ho_2O_3$, especially $CeO_2$, $Pr_2O_3$ and $Nd_2O_3$.

The catalysts used in the process according to the invention contain the said oxides of the rare earth metals in a pure form or as an industrially obtainable mixture of the oxides of several rare earth metals. The oxides may be used as such but are preferably used on an inert carrier.

Examples of inert carriers are tablets of $Al_2O_3$, pumice or charcoal, granules of $Al_2O_3$, pumice or charcoal, aluminum silicate, magnesium silicates, zeolites and $SiO_2$, e.g., silica gel and kieselguhr.

Preferably, carriers based on γ—$Al_2O_3$, boehmite or active charcoal are used. The content of oxides of the rare earth metals, based on the amount of carrier, is not critical and may be varied within wide limits. A content of from 0.2 to 20 percent by weight is advantageous.

This process proves virtually equally successful if instead of an oxide of a rare earth metal, or of a mixture of such oxides, a salt of a rare earth metal or a mixture of such salts is used as a component of the catalyst system.

Suitable cations of the salts to be used according to the invention are all the rare earth metals of which the oxides have been referred to above.

From our observations to date, the chemical nature of the anion has no discernible effect on the success of the process. Accordingly, both inorganic and organic salts may be used, the commercial salts such as the nitrates, sulfates, phosphates, chlorides, carbonates, acetates, oxalates and stearates, especially the nitrates, carbonates, acetates and stearates, being preferred for economic reasons. Suitable organic salts are, in general, the salts of alkylcarboxylic acids, where alkyl is of 1 to 18 carbon atoms, or of α,ω-alkylenedicarboxylic acids, where alkylene is of 2 to 6 carbon atoms, i.e., the compounds already mentioned and, for example, the propionates, butyrates, valerates, succinates and adipates.

The phenolates and toluenesulfonates may also be used. For the purposes of the present invention, the hydroxides, basic oxides, oxy-salts and hydroxy-salts of the rare earth metals also fall under the heading of salts. The hydrates of the salts, which are often readily accessible, may also be employed instead of the pure salts. The weight ratio of the rare earth metal salts of the metals of group VIII of the periodic table should accord broadly with the values stated for the case of the rare earth metal oxides. Since it is evidently only the rare earth metal cations which matter, and the question of whether the anionic radical is oxidic or saline is immaterial, the ratio of rare earth metal oxides to group VIII metals of from 400:1 to 1:150, mentioned for the case of the oxides, must be recalculated in accordance with the molecular weights of the anions of the salts, which are mostly higher. Accordingly, the amount of catalyst mixture is also increased. If for example, in the case of the oxides 10 g of a mixture, containing 9 g of $CeO_2$ and 1 g of Pd, have proved suitable, 21 g of cerium salts would have to be employed in the case of cerium-IV sulfate hydrate ($Ce(SO_4)_2 4H_2O$), and together with the Pd the amount of the catalyst mixture would accordingly be 22 g.

Metals of group VIII of the periodic table are the metals iron (Fe), ruthenium (Ru), osmium (Os), cobalt (Co), nickel (Ni), rhodium (Rh), palladium (Pd), iridium (Ir) and platinum (Pt). Preferred metals of group VIII of the periodic table are Pd, Pt, Ni, Co and Ru, especially Pd and Pt.

The metals of group VIII of the periodic table can also each be used alone, or as mixtures. The metals may be used as such but are preferably used on an inert carrier. The content of metals of group VIII, based on carrier material, is not critical and may be varied within wide limits. Examples of advantageous contents are from 1 to 30 percent by weight for the metals Ni and Ci and from about 0.05 to 5 percent by weight for the remaining metals.

Suitable inert carriers are essentially those mentioned above for the oxides of the rare earth metals, i.e., especially $Al_2O_3$ or charcoal. Of course, it is not necessary for the oxides of the rare earth metals and the metals of group VIII of the periodic table to be supported on identical carriers, nor to be present on one and the same carrier. It is equally possible in the first instance to support the individual active components on separate carriers and only to mix the individual components in the actual reactor.

What is essential for the process according to the invention is that both the oxides of the rare earth metals and the metals of group VIII of the periodic table should be present in sufficient amount in the reactor.

The weight ratio of the oxides of the rare earth metals to the metals of group VIII is not critical. It may be from 400:1 to 1:150; a ratio of from about 200:1 to 1:150, especially from 50:1 to 1:10, is preferred.

The reaction according to the invention is preferably carried out in the liquid phase, and can be carried out either continuously or batchwise. In industrial operation, it is advantageous to use a fixed catalyst bed through which the reactants flow, or to carry out the reaction as a suspension process.

In batchwise operation, the catalyst is advantageously used in amounts of from 0.001 to 100, preferably from 0.01 to 10, percent by weight of active component, based on starting mixture. In continuous operation, the feed rate is advantageously from 0.01 to 100, preferably from 0.1 to 10, liters of starting mixture per liter of catalyst per hour.

In order to achieve reaction temperatures of from 80° to 280° C., preferably from 140° to 220° C., when using low-boiling starting materials, it is necessary to carry out the reaction under a pressure which both counterbalances the vapor pressure of the system and allows the hydrogen required for the hydrogenation to be introduced and reacted. Advantageously, a pressure of from about 15 to 40 bars, preferably from 20 to 30 bars, is used. A higher pressure would not be disadvantageous but is not necessary. The upper limit of pressure is solely dictated by economic considerations.

In this context it is noteworthy that in spite of the presence of metals of group VIII, the decarbonylation side reaction of the aldehyde is virtually not observed at the temperatures required for the reaction, even though this side reaction would have been expected to occur to a substantial degree in view of the disclosures in German Published Application DAS No. 1,917,244 and by H. E. Eschinazi in Bull. Soc. Chim. Fr. 19, (1952) 967. This fact suggests that in the present case the oxides of the rare earth metals have a certain influence on the catalytic activity of the metals of group VIII.

Using the process according to the invention it is possible to manufacture numerous higher ketones, required, for example, as solvents for surface coatings, or as scents, on an industrial scale, with good conversions and good selectivities and hence more simply and more economically than was possible according to the prior art.

EXAMPLE 1

The apparatus used is a 3 l tubular reactor of 4.5 cm diameter, filled with catalyst tablets. The tablets have a diameter of 4 mm and the following composition: 10 percent by weight of Ni, 10 percent by weight of Co and 10 percent by weight of $Nd_2O_3$ (95% pure, the remainder consisting of other rare earth metal oxides) on $\gamma$—$Al_2O_3$. 1 l of a mixture of 62 percent by weight of acetone and 38 percent by weight of methylpropanal per liter of catalyst per hour is passed over the loosely packed catalyst at 180° C. under a total pressure of 18 bars (a $H_2$ atmosphere). The reaction product contains:

| | | |
|---|---|---|
| Acetone | 34.6 | percent by weight |
| Methylpropanal | 6.2 | percent by weight |
| Isopropanol | 0.8 | percent by weight |
| Methylpropanol | 3.4 | percent by weight |
| 4-Methylpentan-2-one | 0.7 | percent by weight |
| 4-Methyl-3-penten-2-one | 0.4 | percent by weight |
| 5-Methylhexan-2-one | 34.3 | percent by weight |
| 5-Methylhexan-2-ol | 0.3 | percent by weight |
| 5-Methyl-3-hexen-2-one | 6.1 | percent by weight |

The composition of the reaction product was determined by analysis by gas chromatography.

EXAMPLE 2

1 liter of a mixture consisting of 65.8 percent by weight of acetone and 34.2 percent by weight of benzaldehyde is passed, per liter of catalyst per hour, at the 3 temperatures shown in the table and under a total pressure of 18 bars (a $H_2$ atmosphere) through the apparatus described in Example 1, which is filled with catalyst tablets consisting of 5 percent by weight of $CeO_2$ (95% $CeO_2$, the remainder being other rare earth metal oxides) and 0.5% of Pd on $\gamma$—$Al_2O_3$. The reaction product contains:

| | 180° C % by weight | 150° C % by weight | 220° C % by weight |
|---|---|---|---|
| Acetone | 49.2 | 58.2 | 45.3 |
| Isopropanol | — | — | 0.5 |
| 4-Methylpentan-2-one | 0.2 | — | 2.5 |
| 4-Methyl-3-penten-2-one | 0.2 | 0.1 | 0.2 |
| Benzaldehyde | 1.4 | 13.2 | 0.8 |
| Benzyl alcohol | 0.4 | — | 2.9 |
| 4-Phenylbutan-2-one | 33.2 | 13.0 | 36.4 |
| 4-Phenylbutan-2-ol | — | — | 0.5 |
| 4-Phenyl-3-buten-2-one (1,5-Diphenylpentan-3-one) | 3.9 | 10.1 | 0.4 |
| (1,5-Diphenyl-1-penten-3-one) (1,5-Diphenyl-1,4-pentadien-3-one) | 5.2 | 3.2 | 6.9 |

EXAMPLE 3

1 liter of a mixture consisting of 68 percent by weight of butan-2-one and 32 percent by weight of n-pentanal is passed, per liter of catalyst per hour, at the total pressure shown in the table (a $H_2$ atmosphere) at 180° C., through the apparatus described in Example 1, which is filled with a catalyst consisting of 5 percent by weight of $Pr_2O_3$ (95% $Pr_2O_3$, the remainder being other rare earth metal oxides) and 0.5 percent by weight of Pd on $\gamma$—$Al_2O_3$.

The reaction product has the following composition:

| | 15 bars % by weight | 18 bars % by weight | 40 bars % by weight |
|---|---|---|---|
| 1-Butene | 0.4 | 0.3 | 0.1 |
| Butan-2-one | 49.4 | 45.2 | 46.1 |
| n-Pentanal | 4.8 | 5.4 | 2.4 |
| n-Pentanol | — | 0.3 | 0.5 |
| Butan-2-ol | — | 0.1 | 0.6 |
| 5-Methyl-heptan-3-one | 0.1 | 0.1 | 1.2 |
| 5-Methyl-4-hepten-3-one | 0.1 | 0.1 | 0.3 |
| Nonan-3-one | | | 8.8 |
| 4-Nonen-3-one | 5.3 | 4.3 | 0.1 |
| 3-Methyl-octan-2-one | — | 0.7 | — |
| 3-Methyl-3-octen-2-one | — | 0.4 | — |
| Nonan-3-ol | — | — | 0.2 |

EXAMPLES 4-11

The examples described below are carried out as follows: 31.3 g of acetone, 12.5 g of n-pentanal and 2 g of a catalyst mixture which consists of equal parts of the catalyst components shown in the table which follows, are heated for two hours at 170° C. under a hydrogen pressure of 30 bars. The product is analyzed by gas chromatography, without taking into account the water which it contains. These experiments of course do not represent optimum conditions and serve to outline the scope of the invention. Example 11 is a Comparative Example in which a catalyst described for aldol condensations (cf., for example, German Laid-Open Application DOS No. 2,150,992) is employed together with Pd. The individual constituents of the reaction product are coded as follows in the table:

A: n-Butene
B: Acetone
C: n-Pentanal
D: Isopropanol
E: 4-Methyl-pentan-2-one
F: 4-Methyl-3-penten-2-one
G: Pentanol
H: Octan-2-one
I: 3-Octan-2-one
J: Octanol

| Ex. | Catalyst | A | B | C | D | E | F | G | H | I | J |
|---|---|---|---|---|---|---|---|---|---|---|---|
| 4 | $Pr_2O_3$ +) 10% Pd/C | 0.6 | 54.7 | 2.7 | — | 0.7 | 1.2 | 0.4 | 35.1 | 4.1 | — |
| 5 | $Nd_2O_3$ +) Ir | 0.1 | 50.1 | 1.9 | — | 0.7 | 2.1 | 1.8 | 37.2 | 4.0 | — |
| 6 | $Gd_2O_3$ +) Pt | 0.2 | 49.6 | 4.7 | — | 1.9 | 1.7 | 1.5 | 28.0 | 12.5 | — |
| 7 | $Sm_2O_3$ +) Ru | 0.4 | 59.9 | 6.4 | — | 0.4 | 1.7 | 2.3 | 29.0 | 1.7 | — |
| 8 | $CeO_2$ Rh | 3.0 | 57.7 | 7.8 | 0.2 | 0.4 | 1.0 | 4.7 | 15.8 | 13.5 | — |
| 9 | $Ho_2O_3$ +) 10% Pd/C | 0.4 | 53.8 | 6.1 | — | 0.8 | 1.2 | 1.3 | 28.4 | 2.6 | — |
| 10 | $La_2O_3$ Pt | 0.1 | 59.1 | 6.7 | — | 0.8 | 1.3 | 1.2 | 20.3 | 8.6 | — |
| 11 | ZnO 10% Pd/C (Comparative Example) | 0.5 | 45.5 | 1.2 | 0.1 | 4.1 | 0.9 | 10.5 | 30.9 | 2.0 | — |

+) 95% of the said oxide, the remainder being other rare earth metal oxides

EXAMPLE 12

A mixture consisting of 73 percent by weight of acetone and 27 percent by weight of 3-methyl-butanal is passed over a catalyst consisting of 5 percent by weight of $Pr_2O_3$ and 0.5 percent by weight of Pd on $\gamma$—$Al_2O_3$, under the reaction conditions described in Example 1.
The reaction product has the following composition:

| i-Butene | 0.1% by weight |
|---|---|
| Acetone | 55.6% by weight |
| 3-Methyl-butanal | 1.6% by weight |
| Isopropanol | 0.1% by weight |
| 3-Methyl-butanol | 0.4% by weight |
| 4-Methyl-pentan-2-one | 0.4% by weight |
| 4-Methyl-3-penten-2-one | 0.1% by weight |
| 6-Methyl-heptan-2-one | 33.0% by weight |
| 6-Methyl-3-hepten-2-one | 1.8% by weight |
| 6-Methylheptan-2-ol | — by weight |

EXAMPLE 13

A mixture of 58 g of acetone and 34 g of 4-methoxybenzaldehyde is heated with 3 g of a catalyst mixture of equal parts of $Pr_2O_3$ and 10% strength Pd/C at 180° C. for 2 hours under a hydrogen pressure of 30 bars. The reaction product is analyzed by gas chromatography. It contains, without taking into account the water formed:

| Acetone | 60.8% by weight |
|---|---|
| 4-Methoxybenzaldehyde | 0.4% by weight |
| 4-Methylpentan-2-one | 3.9% by weight |
| 4-Methyl-3-penten-2-one | 0.5% by weight |
| 4-Methoxybenzyl alcohol | 0.2% by weight |
| 4(4-Methoxyphenyl)-butan-2-one | 25.6% by weight |
| 4(4-Methoxyphenyl)-3-buten-2-one | 4.2% by weight |

EXAMPLE 14

A mixture of 96 g of acetophenone and 15 g of n-butanal is heated with 3 g of a catalyst mixture of equal parts of $Pr_2O_3$ and 10 percent strength by weight Pd/C for 2 hours at 180° C. under a hydrogen pressure of 30 bars. The product contains, without taking into account the water formed:

| Acetophenone | 70.5% by weight |
|---|---|
| n-Butanal | 0.9% by weight |
| n-Butanol | 0.2% by weight |
| 1-Phenylethanol | 0.2% by weight |
| 1-Phenyl-hexanone | 20.2% by weight |
| 1-Phenyl-2-hexenone | 2.1% by weight |

EXAMPLE 15

A mixture of 91 g of 5-methyl-hexan-2-one and 15 g of n-butanal is heated with 3 g of a catalyst mixture of equal parts of $Nd_2O_3$ and 1 percent strength by weight Pt/C for two hours at 180° C. under a hydrogen pressure of 30 bars. The product contains, without taking into account the water formed:

| 5-Methyl-hexan-2-one | 64.5% by weight |
|---|---|
| n-Butanal | 2.8% by weight |
| 5-Methyl-hexan-2-ol | 0.1% by weight |
| n-Butanol | 0.2% by weight |
| 2-Methyl-decan-5-one | 28.3% by weight |
| 2-Methyl-6-decen-5-one | 2.8% by weight |

EXAMPLE 16

A mixture of 58 g of acetone and 30 g of 2-methylbenzaldehyde is heated with 2.5 g of a catalyst mixture of equal parts of $Pr_2O_3$ and 10% strength by weight Pd/C for 2 hours at 180° C. under a hydrogen pressure of 30 bars. The product is analyzed by gas chromatography and contains, without taking into account the water formed:

| Acetone | 52.6% by weight |
|---|---|
| 2-Methyl-benzaldehyde | 4.6% by weight |
| 4-Methylpentan-2-one | 2.1% by weight |
| 4-Methyl-3-penten-2-one | 0.5% by weight |
| 2-Methylbenzyl alcohol | 0.3% by weight |
| Isopropanol | 0.2% by weight |
| 4-(2-Methylphenyl)-butan-2-one | 29.8% by weight |
| 4-(2-Methylphenyl)-3-buten-2-one | 1.7% by weight |

EXAMPLE 17

A mixture of 58 g of acetone and 42.5 g of 4-tert.-butyl-benzaldehyde is heated with 3 g of a catalyst mixture of equal parts of $Nd_2O_3$ and 10% strength by weight Pd/C for 4 hours at 190° C. under a hydrogen pressure of 25 bars. The product is analyzed by gas chromatography and contains, without taking into account the water formed:

| | | |
|---|---|---|
| Acetone | 41.6% | by weight |
| 4-Tert.-butyl-benzaldehyde | 0.6% | by weight |
| 4-Methyl-pentan-2-one | 3.6% | by weight |
| 4-Methyl-3-penten-2-one | 0.8% | by weight |
| 4-Tert.-butyl-benzyl alcohol | 0.6% | by weight |
| Isopropanol | 0.4% | by weight |
| 4-(4-Tert.-butylphenyl)-butan-2-one | 39.2% | by weight |
| 4-(4-Tert.-butylphenyl)-3-buten-2-one | 2.6% | by weight |

EXAMPLE 18

A mixture of 58 g of acetone and 30.5 g of 4-hydroxybenzaldehyde is heated with 3 g of a catalyst mixture of equal parts of $Pr_2O_3$ and 10% strength by weight Pd/C for 2 hours at 180° C. under a hydrogen pressure of 30 bars. The product is analyzed by gas chromatography and contains, without taking into account the water formed:

| | | |
|---|---|---|
| Acetone | 50.8% | by weight |
| 4-Hydroxy-benzaldehyde | 1.0% | by weight |
| 4-Methyl-pentan-2-one | 2.0% | by weight |
| 4-Methyl-3-penten-2-one | 0.4% | by weight |
| 4-Hydroxy-benzyl alcohol | 0.1% | by weight |
| Isopropanol | 0.2% | by weight |
| 4-(4-Hydroxy-phenyl)-butan-2-one | 29.7% | by weight |
| 4-(4-Hydroxy-phenyl)-3-buten-2-one | 2.0% | by weight |

EXAMPLES 19 TO 27

31.3 g of acetone and 12.5 g of n-pentanal are heated in the presence of 2 g of a catalyst mixture of 1 g of a rare earth metal salt and 1 g of a supported catalyst consisting of 90% by weight of active charcoal and 10% by weight of palladium, for two hours at 170° C. under a hydrogen pressure of 30 bars.

The reaction product is examined by gas chromatography, without taking into account the water formed. The table which follows shows the invididual constituents of the reaction products, in percent by weight.

The individual constituents are coded as follows in the table:
A: n-Butene
B: Acetone
C: n-Pentenal
D: Isopropanol
E: 4-Methyl-pentan-2-one
F: 4-Methyl-3-penten-2-one
G: Pentanol
H: Octan-2-one
I: 3-Octen-2-one

| Example | Catalyst | A | B | C | D | E | F | G | H | I |
|---|---|---|---|---|---|---|---|---|---|---|
| 19 | Neodymium oxalate | 0.3 | 61.3 | 12.2 | 0.2 | 0.1 | 2.4 | 2.5 | 15.3 | 1.8 |
| 20 | Neodymium succinate | 0.2 | 59.8 | 12.8 | 0.5 | 0.3 | 1.6 | 1.5 | 16.4 | 0.9 |
| 21 | Neodymium stearate | 0.2 | 52.4 | 0.8 | 0.2 | 0.1 | 1.8 | 0.7 | 33.2 | 1.0 |
| 22 | Lanthanum nitrate | 0.3 | 53.0 | 0.6 | 0.3 | 0.2 | 2.6 | 1.8 | 20.1 | 12.8 |
| 23 | Lanthanum chloride | 0.3 | 57.4 | 9.7 | 0.4 | 0.3 | 3.8 | 1.3 | 17.9 | 1.2 |
| 24 | Praseodymium isovalerate | 0.2 | 54.0 | 2.3 | 0.2 | 0.3 | 2.4 | 1.8 | 23.6 | 6.1 |
| 25 | Neodymium carbonate | 0.2 | 54.6 | 3.6 | 0.2 | 0.4 | 1.8 | 0.7 | 24.3 | 5.2 |
| 26 | Praseodymium acetate | 0.2 | 54.5 | 2.4 | 0.1 | 0.3 | 1.6 | 1.2 | 25.6 | 6.3 |
| 27 | Lanthanum sulfate | 0.3 | 57.2 | 10.3 | 0.3 | 0.4 | 4.2 | 3.1 | 15.2 | 0.7 |

I claim:

1. In a process for the manufacture of a higher ketone by reacting an aldehyde of the formula

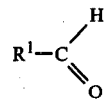

where $R^1$ is unbranched or branched alkyl of 1 to 20 carbon atoms, aryl or cycloalkyl which are unsubstituted or substituted by lower alkyl groups, or aralkyl of 7 to 20 carbon atoms, and the said radicals may also carry one or more hydroxyl or alkoxy groups as inert substitutents, with a ketone of the formula $$CH_3-CO-R^2 \qquad (II)$$

where $R^2$ is unbranched or branched alkyl of 1 to 20 carbon atoms, aryl or cycloalkyl which are unsubstituted or substituted by lower alkyl groups, or aralkyl of 7 to 20 carbon atoms, and the said radicals may also carry one or more hydroxyl or alkoxy groups as inert substituents, in the presence of hydrogen and a catalyst system which possesses both condensing and hydrogenating properties, at an elevated temperature, the improvement which comprises:

carrying out the reaction at from 80° to 280° C. in the presence of a catalyst system which comprises (i) an oxide or a salt of a rare earth metal or a mixture of two or more oxides and/or salts of rare earth metals and (ii) one or more metals of group VIII of the periodic table of the elements, the weight ratio of component (i) to component (ii) of the catalyst system being from 400:1 to 1:150.

2. A process as claimed in claim 1, wherein the reaction is carried out in the presence of a catalyst system which comprises (i) an oxide of a rare earth metal or a mixture of two or more oxides of rare earth metals and (ii) one or more metals of group VIII of the periodic table of the elements.

3. A process as claimed in claim 1, wherein the reaction is carried out in the presence of a catalyst system which comprises (i) a salt of a rare earth metal or a mixture of two or more salts of rare earth metals and (ii) one or more metals of group VIII of the periodic table of the elements.

4. A process as claimed in claim 2, wherein the reaction is carried out in the presence of a catalyst system which contains $Pr_2O_3$ and/or $Nd_2O_3$ and/or $CeO_2$ as component (i).

5. A process as claimed in claim 1, wherein the reaction is carried out in the presence of a catalyst system which contains an oxide or a salt of a rare earth metal or a mixture of oxides and/or salts of rare earth metals as component (i) on an inert carrier.

6. A process as claimed in claim 5, wherein the content of the rare earth metal oxide or oxides on the inert carrier is from 0.2 to 20 percent by weight.

7. A process as claimed in claim 1, wherein the reaction is carried out in the presence of a catalyst system which contains Pd and/or Pt as component (ii).

8. A process as claimed in claim 1, wherein the reaction is carried out in the presence of a catalyst system which contains component (ii) on an inert carrier.

9. A process as claimed in claim 8, wherein the content of component (ii) on the inert carrier is from 0.05 to 30 percent by weight.

10. A process as claimed in claim 5, wherein $Al_2O_3$ or active charcoal is used as the inert carrier.

11. A process as claimed in claim 1, wherein the reaction of the aldehyde of the formula I with the ketone of the formula II is carried out at from 140° to 220° C.

12. A process as claimed in claim 1, wherein the reaction of the aldehyde of the formula I with the ketone of the formula II is carried out in the liquid phase.

13. A process as claimed in claim 1, wherein the weight ratio of component (i) to component (ii) of the catalyst system is from 50:1 to 1:10.

14. A process as claimed in claim 1, wherein the weight ratio of component (i) to component (ii) of the catalyst system is from 200:1 to 1:150.